United States Patent [19]

Yamato et al.

[11] Patent Number: 5,128,369
[45] Date of Patent: Jul. 7, 1992

[54] ARYLALKYLAMINE DERIVATIVES

[75] Inventors: Masatoshi Yamato; Kuniko Hashigaki, both of Okayama; Haruhiko Manabe, Shizuoka; Kenji Ohmori, Mishima, all of Japan

[73] Assignee: Kyowa Hakko Kogyo Co., Ltd., Tokyo, Japan

[21] Appl. No.: 742,074

[22] Filed: Aug. 7, 1991

Related U.S. Application Data

[63] Continuation of Ser. No. 542,069, Jun. 22, 1990, abandoned.

[30] Foreign Application Priority Data

Jun. 23, 1989 [JP] Japan ................................. 1-162021

[51] Int. Cl.$^5$ .................. A61K 31/335; C07D 311/76
[52] U.S. Cl. ...................................... 514/456; 549/407
[58] Field of Search ........................ 514/456; 549/407

[56] References Cited

FOREIGN PATENT DOCUMENTS 344180  9/1976  Austria .
157206  3/1985  European Pat. Off. .
3409612 9/1985  Fed. Rep. of Germany .
2336927 7/1977  France .
2500823 3/1982  France .

OTHER PUBLICATIONS

Chemical Abstracts, vol. 102, No. 17 (1985), 149,043y.
Chemical & Pharmaceutical Bulletin, vol. 36, No. 9 (1988), pp. 3453-3461.
Masatoshi Yamato, et al., Chem. Pharm. Bull., vol. 36, No. 5 (1988) pp. 1785-1765.

Primary Examiner—Nicky Chan
Attorney, Agent, or Firm—Fitzpatrick, Cella, Harper & Scinto

[57] ABSTRACT

Disclosed is a novel arylalkylamine derivative represented by the formula (I)

wherein
X represents —O—, —CH$_2$— or —NR$^3$— in which R$^3$ represents hydrogen or lower alkyl;
Y represents —NH— or $$-N\diagup\diagdown N-CH_2-;$$

Z represents $$-\underset{OR^4}{\underset{|}{CH}}-$$

in which R$^4$ represents hydrogen or lower alkyl or $$-\underset{O}{\underset{\|}{C}}-;$$

Q represents an optionally substituted aryl or optionally substituted aromatic heterocyclic group; each of R$^1$ and R$^2$ independently represents hydrogen or lower alkyl;
each of m and n independently represents an integer of 0 or 1; and
a pharmaceutically acceptable salt thereof. The compound (I) and a pharmaceutically acceptable salt thereof show bronchodilatory and antiallergic activities, and are useful for treating respiratory disorders such as bronchial asthma.

5 Claims, No Drawings

ARYLALKYLAMINE DERIVATIVES

This application is a continuation of application Ser. No. 07/542,069 filed Jun. 22, 1990, now abandoned.

BACKGROUND OF THE INVENTION

The present invention relates to novel arylalkylamine derivatives having bronchodilatory and antiallergic activities. The derivatives are useful for treating respiratory disorders such as bronchial asthma.

Isochroman derivatives having a side chain of arylalkylamine have been known so far. Chem. Pharm. Bull., 36, 1758 (1988) discloses anti-ulcer compounds represented by the following formula (A):

(A)

in which $R^A$ represents hydrogen, methyl, etc. and $R^3$ represents benzyl, phenethyl, etc. EP-A-157206 (Japanese Published Unexamined Patent Application No. 209581/85) discloses a compound exhibiting Ca-antagonizing activity and represented by the following formula (B):

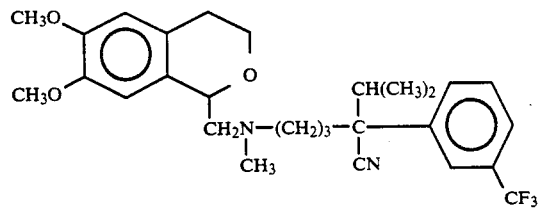
(B)

It is always desired that a novel compound having excellent bronchodilatory and antiallergic activities be developed.

SUMMARY OF THE INVENTION

The object of the present invention is to provide a novel arylalkylamine compound, based on the finding that ethanolamine derivatives having, in the side chain thereof, an isochroman, tetrahydroisoquinoline or tetrahydronaphthalene ring exhibit excellent bronchodilatory and antiallergic activities and are effective as a medicament for treating bronchial asthma.

In accordance with the present invention, there is provided arylalkylamine compounds represented by the following formula (I):

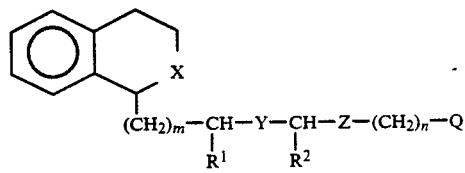
(I)

wherein

X represents —O—, —CH$_2$— or —NR$^3$— in which R$^3$ represents hydrogen or lower alkyl;
Y represents —NH— or

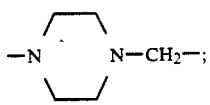

Z represents

in which R$^4$ represents hydrogen or lower alkyl, or

Q represents an optionally substituted aryl or an optionally substituted aromatic heterocyclic group;
each of R$^1$ and R$^2$ independently represents hydrogen or lower alkyl;
each of m and n independently represents 0 or 1 [hereinafter referred to as Compound (I), the same shall apply to compounds with other formula numbers];
or a pharmaceutically acceptable salt thereof.

DETAILED DESCRIPTION OF THE INVENTION

In the definition of Compound (I), the term "lower alkyl" means a straight or branched alkyl having 1 to 6 carbon atoms, and includes, for example, methyl, ethyl, n-propyl, isopropyl, n-butyl, isobutyl, sec-butyl, tertbutyl, n-pentyl, neopentyl, n-hexyl and the like.

The term "aryl" means phenyl or naphthyl. The term "aromatic heterocyclic group" includes, for example, furyl, thienyl, pyridyl and the like. The aryl and aromatic heterocyclic group may contain 1 to 3 substituents. The substituent may be the same or different, and includes, for example, lower alkyl, hydroxyl, lower alkoxyl, halogen (e.g., fluorine, chlorine, bromine and iodine), trifluoromethyl and the like. The lower alkyl and the alkyl moiety in the lower alkoxyl have the same meaning as defined for alkyl.

As the pharmaceutically acceptable salts of Compound (I), mention may be made of inorganic acid salts such as hydrochloride, sulfate and phosphates; and organic acid salts such as acetates, maleates, fumarates, tartrates and citrates.

Compound (I) can be any of possible stereoisomers, including optical isomers and diastereoisomers, as well as a mixture thereof.

Processes for the preparation of Compound (I) are described below.

Process 1

Compound (I) in which Y is —NH— [Compound (Ia)]

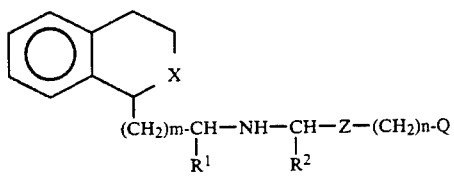
 (Ia)

wherein X, Z, Q, $R^1$, $R^2$, m and n have the same meanings as defined above.

Compound (Ia) is obtained by reducing a Schiff base (IV) obtained by the reaction of a carbonyl Compound (II) set forth below with an amine (III) set forth below.

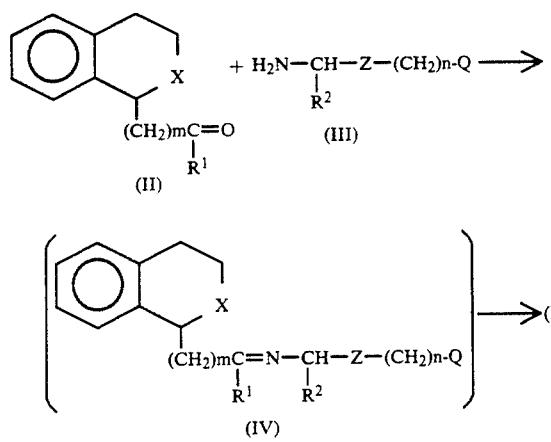

wherein X, Z, Q, $R^1$, $R^2$, m and n have the same meanings as defined above.

Compound (IV) is obtained by the reaction of Compound (II) with Compound (III) in an inert solvent such as methanol. If desired, the reaction is carried out in the presence of a dehydrating agent such as molecular sieves, or by removing water formed during the course of the reaction by means of azeotropy with, e.g., benzene. If desired, Compound (IV) prepared as above is used in the next reaction without being isolated or purified.

Compound (IV) is reduced, e.g., by the use of a reducing agent such as sodium boron hydride, sodium cyanoborohydride and lithium aluminum hydride.

The reaction is carried out in a solvent of a lower alcohol such as methanol and ethanol, at a temperature between 0° C. and the boiling point of the solvent. The reaction usually terminates in 1 to 24 hours.

The starting compounds, Compound (II) and Compound (III), are synthesized according to the processes described in the literature cited in Examples given hereinbelow or according to a process similar to the processes.

Process 2

Compound (I) in which Y is

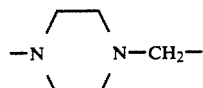

[Compound (Ib)]

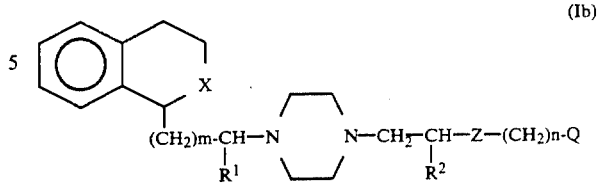
 (Ib)

wherein X, Z, Q, $R^1$, $R^2$, m and n have the same meanings as defined above.

Compound (Ib-1) which is Compound (Ib) in which Z is

is obtained as follows. A carbonyl Compound (VI) set forth below is subjected to a Mannich reaction with a piperazine derivative (V) set forth below.

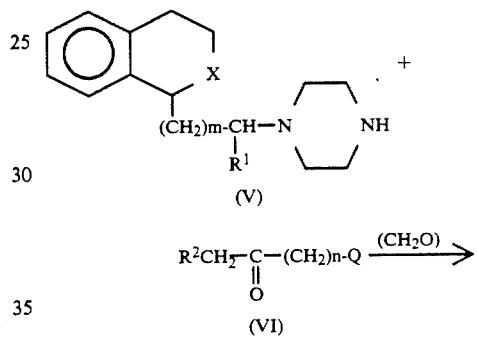

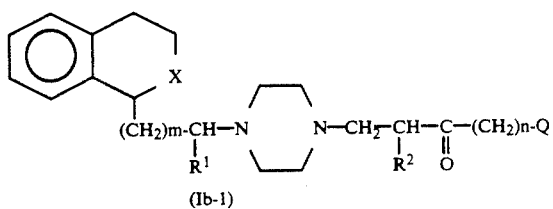

wherein [$CH_2O$] represents formaldehyde or a polymer thereof; and X, Q, $R^1$, $R^2$, m and n have the same meanings as defined above.

Compounds (V) and (VI) are allowed to react with formaldehyde and/or a polymer thereof (e.g., paraformaldehyde) in an inert solvent such as methanol and ethanol in the presence of an acid such as hydrochloric acid. The reaction is carried out at a temperature between room temperature and the boiling point of the solvent and usually terminates in 1 to 48 hours.

The starting compounds Compound (V) and Compound (VI), are synthesized according to the processes described in the literature cited in Examples given hereinbelow or according to similar processes.

Compound (Ib-2), which is Compound (Ib) in which Z is

and is represented by the following formula:

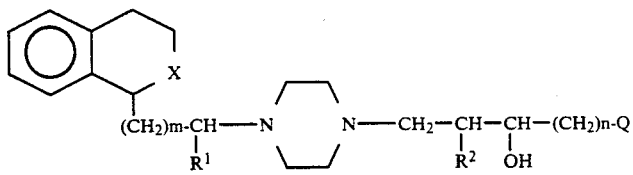

(Ib-2)

wherein X, Q, R¹, R², m and n have the same meanings as defined above, is obtained by subjecting Compound (Ib-1) to a reduction reaction. The reduction is carried out according to the process described in Process 1.

Process 3

Compound (I) in which Z is

[Compound (Ic-1)]

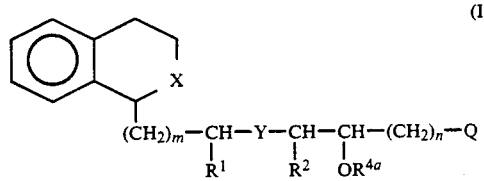

(Ic-1)

wherein $R^{4a}$ represents the same lower alkyl as defined in $R^4$; and X, Y, Q, R¹, R², m and n have the same meanings as defined above.

Compound (Ic-1) is prepared by the reaction of Compound (Ic-2):

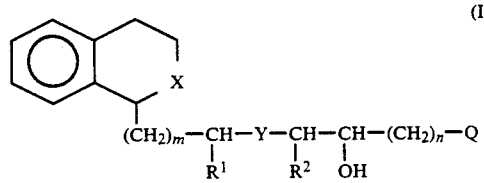

(Ic-2)

wherein X, Y, Q, R¹, R², m and n have the same meanings as defined above, with a lower alcohol (VII):

$$R^{4a}OH \quad (VII)$$

wherein $R^{4a}$ has the same meaning as defined above, at a temperature of $-20°$ C. to room temperature in the presence of an acid catalyst. Compound (Ic-2) is obtained according to the method described in Process 1 or 2. As the acid catalyst, hydrogen chloride gas, hydrogen bromide gas and Lewis acid such as zinc chloride are mentioned. Compound (VII) also uses as a solvent.

The intermediates and the desired compounds prepared in the above preparations are isolated and purified according to the process usually employed in organic synthetic chemistry, for example, filtration, extraction, washing, drying, concentration, recrystallization, various chromatographies and the like. If desired, the intermediates are used in the subsequent reactions without purification.

In the case where Compound (I) is obtained in a free form and its salt form is desired, the free form may be converted into a salt form by a conventional method. In case where Compound (I) is obtained in a salt form and the salt form is desired, the salt form is purified as it is.

Compound (I) and pharmaceutically acceptable salts thereof may be in the form of an addition product with water or various solvents. Such addition products are also included within the scope of the present invention.

Representative compounds of Compound (I) obtained by the Processes are shown in Table 1.

TABLE 1

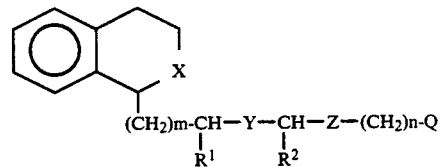

| Compound No. | X | m | R¹ | Y | R² | Z | n | Q |
|---|---|---|---|---|---|---|---|---|
| 1 | 0 | 1 | CH₃ | NH | H | —CH—<br>\|<br>OH | 0 | ⟨phenyl⟩—OH |
| 2 | " | " | " | " | " | H<br>\|<br>—C—<br>\|<br>OH | " | ⟨phenyl⟩—OH |

TABLE 1-continued
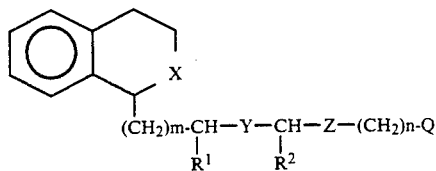
(CH₂)m-CH-Y-CH-Z-(CH₂)n-Q
       |     |
       R¹    R²
| Compound No. | X | m | R¹ | Y | R² | Z | n | Q |
|---|---|---|---|---|---|---|---|---|
| 3 | " | " | " | " | " | -C(H)(OH)- (dashed) | " | " |
| 4 | 0 | 1 | CH₃ | NH | H | -CH(OH)- | 0 | phenyl |
| 5 | " | " | " | " | " | -C(H)(OH)- (wedge) | " | " |
| 6 | " | " | " | " | " | -C(H)(OH)- (dashed) | " | " |
| 7 | " | " | " | " | " | -CH(OH)- | " | 3-hydroxyphenyl |
| 8 | " | " | " | " | " | " | " | 2-hydroxyphenyl |
| 9 | " | " | " | " | " | " | " | 3,5-dihydroxyphenyl |
| 10 | " | " | " | " | " | " | " | 4-methoxyphenyl |
| 11 | " | " | " | " | " | " | " | 3-methoxyphenyl |
| 12 | 0 | 1 | CH₃ | NH | H | -CH(OH)- | 0 | 2,3-dimethoxyphenyl |

TABLE 1-continued
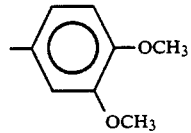
| Compound No. | X | m | R¹ | Y | R² | Z | n | Q |
|---|---|---|---|---|---|---|---|---|
| 13 | " | " | " | " | " | " | " | 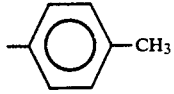 |
| 14 | " | " | " | " | " | " | " | 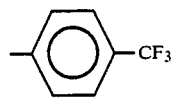 |
| 15 | " | " | " | " | " | " | " | 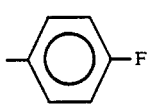 |
| 16 | " | " | " | " | " | " | " | 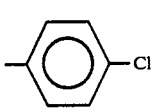 |
| 17 | " | " | " | " | " | " | " | 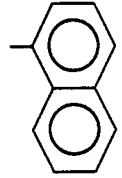 |
| 18 | " | " | " | " | " | " | " | 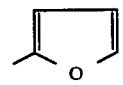 |
| 19 | " | " | " | " | " | " | " | 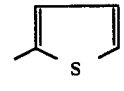 |
| 20 | " | " | " | " | " | " | " | 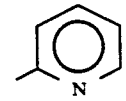 |
| 21 | " | " | " | " | " | " | " | 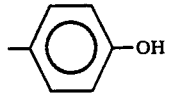 |
| 22 | " | 0 | " | " | " | " | " | 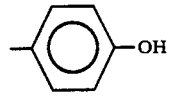 |
| 23 | 0 | 1 | H | NH | H | —CH—<br>    OH | 0 | 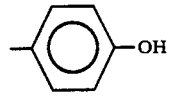 |

TABLE 1-continued

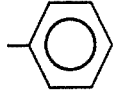

$$(CH_2)_m-CH-Y-CH-Z-(CH_2)_n-Q$$
$$\quad\quad\quad\quad | \quad\quad\quad | $$
$$\quad\quad\quad\quad R^1 \quad\quad\; R^2$$

| Compound No. | X | m | R¹ | Y | R² | Z | n | Q |
|---|---|---|---|---|---|---|---|---|
| 24 | " | " | CH₃ | " | CH₃ | " | " | " |
| 25 | " | " | " | " | H | —CH—<br>\|<br>OCH₃ | " | " |
| 26 | " | " | " | " | " | —CH—<br>\|<br>OH | 1 | 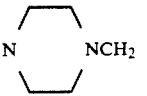 |
| 27 | " | 0 | H | /N\_NCH₂\ | CH₃ | —C—<br>\|\|<br>O | 0 | " |
| 28 | " | " | " | " | H | " | " | " |
| 29 | " | " | " | " | " | —CH—<br>\|<br>OH | " | " |
| 30 | CH₂ | 1 | CH₃ | NH | " | " | " | 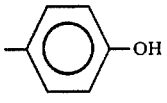 |
| 31 | NCH₃ | " | " | " | " | " | " | " |

The bronchodilatory and antiallergic effects of Compound (I) are investigated in (a) Schultz-Dale reaction and (b) PCA test.

EXPERIMENTAL EXAMPLE 1

Effects on passive Schultz-Dale reaction (bronchodilatory effects)

Male Hartley guinea pigs weighing 350 to 500 g were passively sensitized by intraperitoneal injection of rabbit anti-egg white albumin (EWA) serum prepared by the method of Koda, et al. [Folia pharmacol, Japon 66, 237, (1970)]. After 24 hours, the guinea pigs were stunned and exsanguinated, and then tracheae were removed. The zig-zag strips of the tracheae were prepared by the method of Emmerson, et al. [J. Pharm. Pharmacol.,31, 798, (1979)]. The strips were suspended in Krebs-Henseleit solution at 37° C. airated with 95% $O_2$ and 5% $CO_2$, and equilibrated for one hour. The contraction was induced by adding antigen (EWA, final concentration; 1 μg/ml) and measured by isotonictrasducer (TD-112s, Nihon Kohden, Japan) and recorded on a recorder (Type 3066, Yokogawa-Hokushin Denki, Japan). After the contraction reached stable plateau, the compounds were cumulatively added in order to get concentration-relaxation curves. Concentration of compounds to produce 50% relaxation ($IC_{50}$) was calculated from the regression curve, obtained from cumulative concentration-relaxation response. The results are shown in Table 2.

EXPERIMENTAL EXAMPLE 2

Antiallergic effects:

Antiallergic effects of compounds were studied by passive cutaneous anaphylaxis (PCA) test in rats. Male Wistar rats weighing 180 to 220 g were used for collection of antiserum and Male Wistar rats weighing 120 to 140 g for PCA test.

(A) Preparation of anti-EWA serum in rat

Anti-EWA rat serum was prepared by the method of Stotland, et al [Can. J. Physiol. Pharmacol., 52, 1114, (1974)] as follows. That is, 1 mg of EWA, 20 mg of aluminium hydroxide gel and 0.5 ml of mixed vaccine of pertussis, diphtheria and tetanus were mixed, and the mixture was subcutaneously injected in four foodpads of rats. After 14 days, the blood of sensitized rats was collected from the carotid artery. The serum was separated by centrifugation from collected blood, and stored at $-80°$ C. The 48 hour homologous PCA titer of the serum was 1 :64.

(B) Effects on 48 hour-homologous PCA tests in rats

Three rats in each group were passively sensitized with 8 hold diluted anti-EWA serum (0.05 ml) intradermally injected in two sites of shaved dosal area of rats. After 47 hours, the test compound or its solvent (saline or CMC solution) was orally administrated, and 1 hour thereafter, PCA reaction was induced by intravenous administration of 1% Evan's blue in saline (0.5 ml/100 g) containing 2 mg of EWA. After 30 minutes, animals were sacrificed by bleeding and dorsal skin was stripped to determine the leakage of dye at blue spots, by the method of Katayama et al. [Microbiol. Immunol., 22, 89 (1978)]. The blue-dyed spots were dissected and placed in a test tube containing 1 ml of 1N sodium hydroxide and incubated at 37° C. for 48 hours. Then, 9 ml of a mixture of 0.6N phosphate:acetone (5:13) was added thereto. After shaking, the mixture was centrifuged at 2500 rpm for 10 minutes. A supernatant was separated, and extravasated dye in the supernatant was determined photometrically at 620 nm.

Inhibition percent was calculated as follows:

$$\text{Inhibition (\%)} = \frac{\text{Mean of extravasated dye of solvent-administrated group} - \text{Mean of extravasated dye of test compound-administrated animal}}{\text{Mean of extravasated dye of solvent-administrated group}} \times 100$$

Cases where the inhibition (%) is 50% or higher, were regarded as positive cases, and the minimum administrated dosage, where a positive case was observed in at least one of three animals was regarded as minimum effective dosage (MED).

The results are shown in Table 2.

EXPERIMENTAL EXAMPLE 3

Acute toxicity

The compounds were orally administrated (po) or intraperitoneally administrated (ip) to three male dd-mice weighing 20±1 g. Minimum lethal dose (MLD) was determined by observing the mortality for seven days after the administration. The results are shown in Table 2.

TABLE 2

| Test Compound | Broncho-dilatory effect $IC_{50}$ (M) | Anti-PCA MED (mg/kg) | Acute Toxicity MLD (mg/kg) | |
|---|---|---|---|---|
| | | | po | ip |
| 1 | $1.28 \times 10^{-8}$ | 10 | >300 | >100 |
| 2 | $6.12 \times 10^{-10}$ | 10 | >300 | >100 |
| 3 | $2.76 \times 10^{-9}$ | NE | NT | NT |
| 4 | $2.60 \times 10^{-7}$ | 10 | 200 | 100 |
| 5 | $1.90 \times 10^{-8}$ | 1 | 200 | 25 |
| 6 | $1.20 \times 10^{-5}$ | NE | 200 | >100 |
| 7 | $1.10 \times 10^{-8}$ | 10 | 300 | 100 |
| 8 | $5.3 \times 10^{-8}$ | NE | 200 | 100 |
| 9 | $1.18 \times 10^{-9}$ | NT | 200 | NT |
| 10 | $8.10 \times 10^{-8}$ | 10 | 200 | 100 |
| 16 | $6.14 \times 10^{-8}$ | NE. | 300 | >100 |
| 17 | $3.40 \times 10^{-6}$ | 1 | 100 | 100 |
| 20 | $3.61 \times 10^{-8}$ | NE | >300 | >100 |
| 23 | $8.76 \times 10^{-9}$ | NT | NT | NT |
| 24* | $1.60 \times 10^{-6}$ | NE | >300 | >100 |
| 25 | $2.40 \times 10^{-9}$ | NE | NT | NT |
| 26 | $9.04 \times 10^{-6}$ | NE | NT | NT |
| 30 | $1.95 \times 10^{-9}$ | 10 | >300 | >100 |
| 31 | $8.50 \times 10^{-8}$ | NE | >300 | >100 |

NT: not done
NE: no effect
*represents hydrochloride of the compound.

Compound (I) or pharmaceutically acceptable salts thereof may be used as they are or in the form of various dosage forms depending upon their pharmacological activity and purpose of administration. The medical preparation of the present invention is prepared by uniformly mixing, as an active ingredient, an effective dose of Compound (I) or pharmaceutically acceptable salts thereof with pharmaceutically acceptable carriers.

The suitable carrier is selected from a broad range of carriers depending upon preparation modes desired for administration. These medical compositions are desirably in the form of unit dose suited to oral administration.

In preparing compositions which are in the form suitable for oral administration, any useful pharmaceutically acceptable carriers are used. A liquid preparation suited to oral administration, for example, an emulsion and a syrup are prepared using water; sugars such as sucrose, sorbitol, fructose, etc.; glycols such as polyethylene glycol, propylene glycol, etc.; oils such as sesame oil, olive oil, soybean oil, etc.; antiseptics such as an alkyl p-hydroxybenzoate, etc.; flavors such as strawberry flavor, pepper mint, etc. Furthermore, a powder, a pill, a capsule and a tablet are prepared by using an excipient such as lactose, glucose, sucrose, mannitol, etc.; a disintegrator such as starch, sodium alginate, etc.; a lubricant such as magnesium stearate, talc, etc.; a binder such as polyvinyl alcohol, hydroxypropyl cellulose, gelatin, etc.; a surfactant such as a fatty acid ester, etc.; a plasticizer such as glycerine, etc. A tablet and a capsule are the most useful unit preparations for oral administration since their administration is easy. Upon preparing the tablet and capsule, individual pharmaceutical carriers are used.

Furthermore, Compound (I) is administrated by inhalation in the form of aerosol, finely pulverized powders, or spray solution. In the case of aerosol administration, the present compound is dissolved in an appropriately pharmaceutically acceptable solvent, for example, ethyl alcohol or a combination of miscible solvents and then mixed with a pharmaceutically acceptable propellant. The aerosol composition is used by filling it in a pressure-withstanding container composition. It is preferable that the aerosol valve is a metering valve for discharging an effective dosage of aerosol composition as determined in advance. The effective dose and dosage regimen of Compound (I) or pharmaceutically acceptable salts thereof vary depending on mode of administration and, age, body weight, conditions, etc. of the patient. Daily dose is generally 0.01 to 1 mg/60 kg and the number of administration per day is 2 to 3 times.

Hereafter, the present invention is described by referring to Examples and Reference Examples below.

EXAMPLE 1

1-(4-Hydroxyphenyl)-2-[2-(isochroman-1-yl)-1-methylethylamino]ethanol (Compound 1)

In 15 ml of anhydrous methanol were dissolved 2.93 g (15.5 mmol) of (isochroman-1-yl)acetone [Chem. Pharm. Bull., 36, 1758 (1988)] and 1.57 g (10.3 mmol) of 2-amino-1-(4-hydroxyphenyl)ethanol [U.S. Pat. No. 2,585,988 (1952)], and the resulting solution was stirred for 3 hours at room temperature. Methanol was evaporated, and anhydrous benzene was added to the mixture, and water formed was removed off by azeotropic distillation. To the resulting mixture was added 15 ml of anhydrous methanol. Subsequently, 567 mg (15 mmol) of sodium borohydride was gradually added under ice cooling, and the resulting mixture was stirred for 3 hours at room temperature. The methanol was evaporated off, and then 10% sulfuric acid aqueous solution was added to the residue, and the mixture was washed with ether. The resulting mixture was rendered basic with the addition of saturated aqueous potassium hydrogencarbonate and then extracted with ethyl acetate.

The ethyl acetate layer was washed with water and then dried over anhydrous magnesium sulfate. The solvent was evaporated off, and the residue was subjected to silica gel column chromatography (ethyl acetate :triethylamine=20:1) to give 2.8 g (83%) of crystals of Compound 1.

Melting point: 83°–105° C.

Elementary analyses: as $C_{20}H_{25}NO_3$ Found (%): C, 73.49, H, 7.62, N, 4.20 Calcd. (%): C, 73.37, H, 7.70, N, 4.28

FAB-MS (m/e): 328($M^+ +1$)

IR (nujol) $cm^{-1}$: 3280

NMR ($CDCl_3 + DMSO-d_6$) δ: 1.08 and 1.19(3H, d, J=6.0 Hz), 1.63–2.38(2H, m), 2.38–3.22(5H, m), 3.38–4.13(2H, m), 4.31–4.90(2H, m), 5.33(3H, s), 6.65(2H, d, J=8.0 Hz), 6.95(4H, s), 7.05(2H, d, J=8.0 Hz)

EXAMPLE 2

(1R)-1-(4-hydroxyphenyl)-2-[2-(isochroman-1-yl)-1-methylethylamino]ethanol (Compound 2)

Compound 2 was obtained as a powder in the same manner as in Example 1, using (isochroman-1-yl)acetone and (R)-2-amino-(4-hydroxyphenyl)ethanol [J. Med. Chem., 7, 569 (1964)]. The yield of the compound was 82%.

$[\alpha]_D^{24} = -27.6°$ (c=1, ethanol)

Data of MS, IR and NMR analyses coincided with those of Compound 1.

EXAMPLE 3

(1S)-1-(4-hydroxyphenyl)-2-[2-(isochroman-1-yl)-1-methylethylamine]ethanol (Compound 3)

Compound 3 was obtained as a powder in the same manner as in Example 1, using (isochroman-1-yl)acetone and (S)-2-amino-1-(4-hydroxyphenyl)ethanol [J. Med. Chem., 7, 569 (1964)]. The yield of the compound was 75%.

$[\alpha]_D^{24} = +22.6°$ (c=1, ethanol)

Data of MS, IR and NMR analyses coincided with those of Compound 1.

EXAMPLE 4

2-[2-(Isochroman-1-yl)-1-methylethylamino]-1-phenylethanol (Compound 4)

Compound 4 was obtained as crystals in the same manner as in Example 1, using (isochroman-1-yl)acetone and 2-amino-1-phenylethanol [Farmaco. Ed. Sci., 8, 86 (1953)]. The yield of the compound was 55%.

Melting point: 80°–105° C.

Elementary analyses: as $C_{20}H_{25}NO_2$ Found (%): C, 77.09, H, 8.06, N, 4.49 Calcd. (%): C, 77.14, H, 8.09, N, 4.50

FAB-MS (m/e): 312($M^+ +1$)

IR (nujol) $cm^{-1}$: 3280

NMR ($CDCl_3$) δ: 1.16 and 1.25(3H, d, J=6.0 Hz), 1.83–2.16(2H, m), 2.65–3.21(5H, m), 3.08(3H, s), 3.48–4.35(2H, m), 4.60–5.10(2H, m), 7.15(4H, s), 7.36 (5H, s)

EXAMPLE 5

(1R)-2-[2-(Isochroman-1-yl)-1-methylethylamino]-1-phenylethanol (Compound 5)

Compound 5 was obtained as crystals in the same manner as in Example 1, using (isochroman-1-yl)acetone and (R)-(-)-2-amino-1-phenylethanol [J. Org. Chem., 45, 2785 (1980)]. The yield of the compound was 63%.

Melting point: 83°–107° C.

$[\alpha]_D^{21} = -34.0°$ (c=1, ethanol)

Data of MS, IR and NMR analyses coincided with those of Compound 4.

EXAMPLE 6

(1S)-2-[2-(Isochroman-1-yl)-1-methylethylamino]-1-phenylethanol (Compound 6)

Compound 6 was obtained as crystals in the same manner as in Example 1, using (isochroman-1-yl)acetone and (S)-(+)-2-amino-1-phenylethanol [J. Org. Chem., 45, 2785 (1980)]. The yield of the compound was 39%.

Melting point: 84°–110° C.

$[\alpha]_D^{21} = +48.0°$ (c=1, ethanol)

Data of MS, IR and NMR analyses coincided with those of Compound 4.

EXAMPLE 7

1-(3-Hydroxyphenyl)-2-[2-(isochroman-1-yl)-1-methylethylamino]ethanol (Compound 7)

Compound 7 was obtained as a powder in the same manner as in Example 1, using (isochroman-1-yl)acetone and 2-amino-1-(3-hydroxyphenyl)ethanol [J. Chem. Soc., 4576 (1961)]. The yield of the compound was 58%.

Elementary analyses: as $C_{20}H_{25}NO_3$ Found (%): C, 73.44, H, 7.66, N, 4.21 Calcd. (%): C, 73.37, H, 7.70, N, 4.28

FAB-MS (m/e): 328($M^+ +1$)

IR (nujol) $cm^{-1}$: 3180

NMR ($CDCl_3$) δ: 1.15 and 1.24(3H, d, J=6.0 Hz), 1.71–2.14(2H, m), 2.40–3.35(5H, m), 3.41–4.28(2H, m), 4.42–5.03(2H, m), 5.13(3H, s), 6.50–7.30(5H, m)

EXAMPLE 8

1-(2-Hydroxyphenyl)-2-[2-(isochroman-1-yl)-1-methylethylamino]ethanol (Compound 8)

Compound 8 was obtained as crystals in the same manner as in Example 1, using (isochroman-1-yl)acetone and 2-amino-1-(2-hydroxyphenyl)ethanol [J. Med. Chem., 8, 368 (1965)]. The yield of the compound was 78%.

Melting point: 131°–137° C.

Elementary analyses: as $C_{20}H_{25}NO_3$ Found (%): C, 73.52, H, 7.69, N, 4.19 Calcd. (%): C, 73.37, H, 7.70, N, 4.28

FAB-MS (m/e): 328($M^+ +1$)

IR (nujol) $cm^{-1}$: 3330

NMR ($CDCl_3 + DMSO-d_6$) δ: 1.40 and 1.52(3H, d, J=6.0 Hz), 1.94–2.45(2H, m), 2.59–3.32(5H, m), 3.40–4.45(2H, m), 4.65–5.38(2H, m), 5.82(3H, s), 6.58–7.47(8H, m)

EXAMPLE 9

1-(3,5-Dihydroxyphenyl)-2-[2-(isochroman-1-yl)-1-methylethylamino]ethanol (Compound 9)

Compound 9 was obtained as crystals in the same manner as in Example 1, using (isochroman-1-yl)acetone and 2-amino-1-(3,5-dihydroxyphenyl)ethanol [J. Med. Chem., 9, 273 (1966)]. The yield of the compound was 43%.

Melting point: 96°–103° C.

Elementary analyses: as $C_{20}H_{25}NO_4$ Found (%): C, 69.98, H, 7.50, N, 4.16 Calcd. (%): C, 69.95, H, 7.34, N, 4.08

FAB-MS (m/e): 344(M++1)

IR (nujol) cm$^{-1}$: 3300

NMR (CDCl$_3$+DMSO-d$_6$) δ: 1.12 and 1.20(3H, d, J=6.0 Hz), 1.60-2.27(2H, m), 2.32-3.27(5H, m), 3.32-4.12(2H, m), 4.23-5.11(2H, m), 5.20(4H, s), 5.88-6.22(3H, m), 7.15(4H, s)

EXAMPLE 10

2-[2-(Isochroman-1-yl)-1-methylethylamino]-1-(4-methoxyphenyl)ethanol (Compound 10)

Compound 10 was obtained as crystals in the same manner as in Example 1, using (isochroman-1-yl)acetone and 2-amino-1-(4-methoxyphenyl)ethanol [Arch. Phar., 269, 581 (1931)]. The yield of the compound was 48%.

Melting point: 98°-124° C.

Elementary analyses: as $C_{21}H_{27}NO_3$ Found (%): C, 73.56, H, 7.64, N, 4.01 Calcd. (%): C, 73.87, H, 7.97, N, 4.10

FAB-MS (m/e): 342(M++1)

IR (nujol) cm$^{-1}$: 3340

NMR (CDCl$_3$) δ: 1.43 and 1.54(3H, d, J=6.0 Hz), 2.09-2.51(2H, m), 2.56-3.02(3H, m), 3.02-3.44(2H, m), 3.46-4.45(2H, m), 3.76(3H, s), 4.65-5.11(1H, m), 5.11-5.50(1H, m), 6.79(2H, d, J=8.5 Hz), 7.10(6H, s), 7.34(2H, d, J=8.5 Hz)

EXAMPLE 11

2-[2-(Isochroman-1-yl)-1-methylethylamino]-1-(3-methoxyphenyl)ethanol (Compound 11)

Compound 11 was obtained as an oil in the same manner as in Example 1, using (isochroman-1-yl)acetone and 2-amino-1-(3-methoxyphenyl)ethanol [J. Chem. Soc., 4576 (1961)]. The yield of the compound was 27.4%.

Elementary analyses: as $C_{21}H_{27}NO_3$ Found (%) : C, 73.61, H, 7.84, N, 3.92 Calcd. (%): C, 73.87, H, 7.97, N, 4.10

FAB-MS (m/e): 342(M++1)

IR (CHCl$_3$) cm$^{-1}$: 3320

NMR (CDCl$_3$) δ: 1.13 and 1.16(3H, d, J=6.0 Hz), 1.63-2.16(2H, m), 2.35-3.10(5H, m), 3.13-3.54(2H, br), 3.60-4.31(2H, m), 3.73(3H, s), 4.40-4.99(2H, m), 6 60-7.41(8H, m)

EXAMPLE 12

2-[2-(Isochroman-1-yl)-1-methylethylamino]-1-(2-methoxyphenyl)ethanol (Compound 12)

Compound 12 was obtained as crystals in the same manner as in Example 1, using (isochroman-1-yl)acetone and 2-amino-1-(2-methoxyphenyl)ethanol [J. Med. Chem., 6, 266 (1963)]. The yield of the compound was 43%.

Melting point: 118°-123° C.

Elementary analyses: as $C_{21}H_{27}NO_3$ Found (%): C, 73.57, H, 7.71, N, 3.95 Calcd. (%): C, 73.87, H, 7.97, N, 4.10

FAB-MS (m/e): 342(M++1)

IR (nujol) cm$^{-1}$: 3280

NMR (CDCl$_3$) δ: 1.17 and 1.26(3H, d, J=6.0 Hz), 1.76-2.19(2H, m), 2.59-3.33(5H, m), 3.61-4.31(2H, m), 3.66(3H, s), 4.04(2H, s), 4.59-5.29(2H, m), 6.67-7.68(8H, m)

EXAMPLE 13

2-[2-(Isochroman-1-yl)-1-methylethylamino]-1-(3,4-dimethoxyphenyl)ethanol (Compound 13)

Compound 13 was obtained as a powder in the same manner as in Example 1, using (isochroman-1-yl)acetone and 2-amino-1-(3,4-dimethoxyphenyl)ethanol [Arch. Pharm., 269, 581 (1931)]. The yield of the compound was 21%.

FAB-MS (m/e): 372(M++1)

IR (nujol) cm$^{-1}$: 3330

NMR (CDCl$_3$) δ: 1.17(3H, d, J=6.6 Hz), 1.64-2.13(2H, m), 2.41-3.30(7H, m), 3.56-4.19(2H, m), 3.80(3H, s), 3.89(3H, s), 4.38-5.00(2H, m), 6.71-6.96(3H, m), 7.03(4H, s)

EXAMPLE 14

2-[2-(Isochroman-1-yl)-1-methylethylamino]-1-(4-methylphenyl)ethanol (Compound 14)

Compound 14 was obtained as a powder in the same manner as in Example 1, using (isochroman-1-yl)acetone and 2-amino-1-(4-methylphenyl)ethanol [J. Chem. Soc., 4576 (1961)]. The yield of the compound was 37%.

FAB-MS (m/e): 326(M++1)

IR (nujol) cm$^{-1}$: 3290

NMR (CDCl$_3$) δ: 1.11 and 1.17(3H, d, J=6.0 Hz), 1.63-2.13(2H, m), 2.32(3H, s), 2.60-3.31(7H, m), 3.46-4.36(2H, m), 4.46-5.12(2H, m), 6.96-7.50(8H, m)

EXAMPLE 15

2-[2-(Isochroman-1-yl)-1-methylethylamino]-1-(4-trifluoromethylphenyl)ethanol (Compound 15)

Compound 15 was obtained as an oil in the same manner as in Example 1, using (isochroman-1-yl)acetone and 2-amino-1-(4-trifluoromethylphenyl)ethanol [J. Med. Chem., 6, 266 (1963)]. The yield of the compound was 44%.

FAB-MS (m/e): 380(M++1)

IR (neat) cm$^{-1}$: 3300

NMR (CDCl$_3$) δ: 1.17 and 1.20(3H, d, J=6.0 Hz), 1.69-2.12(2H, m), 2.52-3.32(5H, m), 3.39-4.38(4H, m), 4.52-5.19(2H, m), 7.14(4H, s), 7.27-7.72(4H, m)

EXAMPLE 16

1-(4-Fluorophenyl)-2-[2-(isochroman-1-yl)-1-methylethylamino]ethanol (Compound 16)

Compound 16 was obtained as a powder in the same manner as in Example 1, using (isochroman-1-yl)acetone and 2-amino-1-(4-fluorophenyl)ethanol [Chem. Ber., 88, 1267 (1955)]. The yield of the compound was 35%.

FAB-MS (m/e): 330(M++1)

IR (nujol) cm$^{-1}$: 3300 and 3330

NMR (CDCl$_3$) δ: 1.11 and 1.18(3H, d, J=6.0 Hz), 1.61-2.10(2H, m), 2.42-3.48(7H, m), 3.48-4.30(2H, m), 4.47-5.12(2H, m), 6.78-7.51(8H, m)

EXAMPLE 17

1-(4-Chlorophenyl)-2-[2-(isochroman-1-yl)-1-methylethylamino]ethanol (Compound 17)

Compound 17 was obtained as a powder in the same manner as in Example 1, using (isochroman-1-yl)acetone and 2-amino-1-(4-chlorophenyl)ethanol [J. Am. Chem. Soc., 74, 5514 (1952)]. The yield of the compound was 38%.

FAB-MS (m/e): 346(M$^+$+1)

IR (nujol) cm$^{-1}$: 3080 and 3280

NMR (CDCl$_3$) δ: 1.07 and 1.12(3H, d, J=6.0Hz), 1.62–2.05(2H, m), 2.35–3.28(5H, m), 3.24(2H, s), 3.43–4.28(2H, m), 4.45–4.97(2H, m), 7.09(4H, s), 7.24 (4H, s)

EXAMPLE 18

2-[2-(Isochroman-1-yl)-1-methylethylamino]-1-(2-naphthyl)ethanol (Compound 18)

Compound 18 was obtained as an oil in the same manner as in Example 1, using (isochroman-1-yl)acetone and 2-amino-1-(2-naphthyl)ethanol [J. Med. Chem., 12, 452 (1969)]. The yield of the compound was 55%.

Elementary analyses: as C$_{24}$H$_{27}$NO$_2$ Found (%): C, 83.38, H, 7.58, N, 3.96 Calcd. (%): C, 83.44, H, 7.89, N, 4.06

IR (neat) cm$^{-1}$: 3310 and 3400

NMR (CDCl$_3$) δ: 1.11 and 1.20(3H, d, J=6.0 Hz), 1.74–2.13(2H, m), 2.50–3.32(7H, m), 3.45–4.37(2H, m), 4.65–5.20(1H, m), 5.29–5.65(1H, m), 6.85–8.23 (11H, m)

EXAMPLE 19

1-(2-Furyl)-2-[2-(isochroman-1-yl)-1-methylethylamino]ethanol (Compound 19)

Compound 19 was obtained as a powder in the same manner as in Example 1, using (isochroman-1-yl)acetone and 2-amino-1-(2-furyl)ethanol [Zh. Organ. Khim., 1, 541 (1965)]. The yield of the compound was 45%.

FAB-MS (m/e): 302(M$^+$+1)

IR (nujol) cm$^{-1}$: 3290

NMR (CDCl$_3$) δ: 1.07 and 1.14(3H, d, J=6.0 Hz), 1.16–2.10(2H, m), 2.55–3.18(7H, m), 3.41–4.32(2H, m), 4.49–5.08(2H, m), 6.13–6.40(2H, m), 6.88–7.40(5H, m)

EXAMPLE 20

2-[2-(Isochroman-1-yl)-1-methylethylamino]-1-thienylethanol (Compound 20)

Compound 20 was obtained as an oil in the same manner as in Example 1, using (isochroman-1-yl)acetone and 2-amino-1-thienylethanol [J. Org. Chem., 18, 21 (1953)]. The yield of the compound was 61%.

FAB-MS (m/e): 318(M$^+$+1)

IR (neat) cm$^{-1}$: 3300 and 3350

NMR (CDCl$_3$) δ: 1.07 and 1.14(3H, d, J=6.0 Hz), 1.54–2.07(2H, m), 2.59–3.34(7H, m), 3.43–4.31(2H, m), 4.59–5.10(2H, m), 6.75–7.30(7H, m)

EXAMPLE 21

2-[2-(Isochroman-1-yl)-1-methylethylamino]-1-(2-pyridyl)ethanol (Compound 21)

Compound 21 was obtained as an oil in the same manner as in Example 1, using (isochroman-1-yl)acetone and 2-amino-1-(2-pyridyl)ethanol [Arch. Pharm., 291, 12 (1958)]. The yield of the compound was 51%.

FAB-MS (m/e): 313(M$^+$+1)

IR (neat) cm$^{-1}$: 3300 and 3400

NMR (CDCl$_3$) δ: 1.11 and 1.20(3H, d, J=6.0 Hz), 1.75–2.07(2H, m), 2.62–3.30(5H, m), 3.31(2H, s), 3.76–4.28(2H, m), 4.62–5.10(2H, m), 6.88–7.86(3H, m), 7.08(4H, s), 8.52(1H, dd, J=1.0, 5.2 Hz)

EXAMPLE 22

1-(4-Hydroxyphenyl)-2-[1-(isochroman-1-yl)ethylamino]ethanol (Compound 22)

Compound 22 was obtained as a powder in the same manner as in Example 1, using 1-acetylisochroman [Arm. Khim. Zh., 32, 397 (1979)]and 2-amino-1-(4-hydroxyphenyl)ethanol hydrochloride. The yield of the compound was 68%.

FAB-MS (m/e): 314(M$^+$+1)

IR (CHCl$_2$) cm$^{-1}$: 3310 and 3500

NMR (CDCl$_3$) δ: 0.77(0.75H, d, J=6.0 Hz), 1.17(2.25H, d, J=6.0 Hz), 2.22–3.25(5H, m), 3.45–3.87(1H, m), 3.87–4.15(1H, m), 4.18–4.78(2H, m), 4.59(3H, s), 6.50(2H, d, J=8.0 Hz), 6.83(2H, d, J=8.0Hz), 6.97 (4H, s)

EXAMPLE 23

1-(4-Hydroxyphenyl)-2-[2-(isochroman-1-yl)ethylamino]ethanol (Compound 23)

Compound 23 was obtained as a powder in the same manner as in Example 1, using (isochroman-1-yl)acetoaldehyde [Chem. Pharm. Bull., 36, 1758 (1988)]and 2-amino-1-(4-hydroxyphenyl)ethanol hydrochloride. The yield of the compound was 55%.

FAB-MS (m/e): 314(M$^+$+1)

IR (nujol) cm$^{-1}$: 3280

NMR (CDCl$_3$) δ: 1.74–2.30(2H, m), 2.35–3.04(6H, m), 3.36–4.10(2H, m), 4.38–5.08(2H, m), 5.00(3H, s), 6.67(2H, d, J=8.0 Hz), 6.80–7.32(6H, m)

EXAMPLE 24

1-(4-Hydroxyphenyl)-2-[2-(isochroman-1-yl)-1-methylethylamino]-1-propanol (Compound 24)

An oily product was obtained in the same manner as in Example 1, using (isochroman-1-yl)acetone and 2-amino-1-(4-hydroxyphenyl)-1-propanol [J. Med. Chem., 14, 148 (1971)]. The product was dissolved in anhydrous methanol, and concentrated hydrochloric acid was added thereto. The solvent was evaporated off to give a hydrochloride. The hydrochloride was then washed with ether to give Compound 24 as crystals in a yield of 72%.

The spectral data set forth below were determined in the form of free base.

Melting point: 99°–103° C.

FAB-MS (m/e): 342(M$^+$+1)

IR (nujol) cm$^{-1}$: 3190 and 3280

NMR (CDCl$_3$) δ: 0.85(3H, d, J=6.0 Hz), 1.16(3H, d, J=6.0 Hz), 1.64–2.30(2H, m), 2.33–3.36(4H, m), 3.57–4.30(2H, m), 4.34–4.96(5H, m), 6.67(2H, d, J=8.0 Hz), 6.90–7.35(6H, m)

EXAMPLE 25

2-(4-Hydroxyphenyl)-N-[2-(isochroman-1-yl)-1-methylethylamino]-2-methoxyethylamine (Compound 25)

In anhydrous methanol was dissolved 1.2 g (3.67 mmol) of 1-(4-hydroxyphenyl)-2-[2-(isochroman-1-yl)-1-methylethylamino]ethanol obtainable by Example ', and then dried hydrogen chloride gas was passed through the solution for 5 minutes at 0° C. The methanol was evaporated off under reduced pressure, and saturated potassium bicarbonate solution was added to the residue. The mixture was extracted with ethyl acetate, and the extract was washed with water and then dried. The solvent was evaporated to give 1.13 g (yield: 90%) of amorphous powders of Compound 25.

IR (nujol) cm$^{-1}$: 3380

NMR (CDCl$_3$+DMSO-d$_6$) δ: 1.08 and 1.17(3H, d, J=6 Hz), 1.64–2.15(2H, m), 2.38–3.26(5H, m), 3.14(3H, s), 3.44–4.33(3H, m), 4.39–5.19(3H, m), 6.68(2H, d, J=8 Hz), 6.82–7.23(6H, m)

EXAMPLE 26

1-[2-(Isochroman-1-yl)-1-methylethylamino]-3-phenyl-2-propanol (Compound 26)

Compound 26 was obtained as an oily in the same manner as in Example 1, using (isochroman-1-yl)acetone and 1-amino-3-phenyl-2-propanol [J. Org. Chem., 46, 4051 (1981)].

FAB-MS (m/e): 326(M$^+$ +1)

IR (neat) cm$^{-1}$: 3310

NMR (CDCl$_3$) δ: 0.94 and 1.00(3H, d, J=6.0 Hz), 1.69–2.09(2H, m), 2.39–3.15(9H, m), 3.58–4.40(3H, m), 4.59–5.17(1H, m), 6.99(4H, s), 7.12(5H, s)

EXAMPLE 27

3-{4-[(Isochroman-1-yl)methyl]piperazin-1-yl}-2-methylphenylpropanone (Compound 27)

In 10 ml of anhydrous ethanol were dissolved 0.33 g (1.4 mmol) of 1-[(isochroman-1-yl)methyl]piperazine obtainable by Reference Example 2, 0.23 g (1.7 mmol) of propiophenone and 2 ml of concentrated hydrochloric acid. To the resulting solution was added 75 mg (2.5 mmol) of paraformaldehyde. The mixture was heated under reflux for 30 hours, during which the same amount of paraformaldehyde was added three times at intervals of 7 hours. The ethanol was evaporated off, and the residue obtained was recrystallized from a mixture of methanol and ether to give 0.36 g (yield: 53%) of hydrochloride of Compound 27.

Melting point: 220°–226° C.

Elementary analyses: as C$_{24}$H$_{30}$N$_2$O$_2$ Found (%): C, 63.10, H, 6.86, N, 6.41 Calcd. (%): C, 62.85, H, 6.57, N, 6.43

DI-MS (m/e): 378(M$^+$)

IR (nujol) cm$^{-1}$: 1680

NMR (CDCl$_3$) δ: 1.25(3H, d, J=7 Hz), 2.10–2.30(15H, m), 3.50–4.20(2H, m), 4.80–5.20(1H, m), 6.88–7.80(7H, m), 7.98(2H, dd, J=8.2 Hz)

EXAMPLE 28

3-{4-[(Isochroman-1-yl)methyl]piperazin-1-yl}-1-phenylpropanone (Compound 28)

Dihydrochloride of Compound 28 was obtained in the same manner as in Example 27, using 1-[(isochroman-1-yl)methyl]piperazine and acetophenone. The yield of the dihydrochloride of the compound was 71%.

Melting point: 228°–230° C. (decomp.)

IR (nujol) cm$^{-1}$: 1680

NMR (CDCl$_3$) δ: 2.71–3.00(2H, m), 3.15–3.50(2H, m), 3.55–4.15(14H, m), 5.10–5.60(1H, m), 7.10–7.40 (4H, m), 7.45–7.80(3H, m), 7.90–8.20(2H, m)

EXAMPLE 29

3-{4-[(Isochroman-1-yl)methyl]piperazin-1-yl}-1-phenylpropanol (Compound 29)

Hydrochloride of Compound 29 was obtained in the same manner as in Example 1, using 3-{4-[(isochroman-1-yl)methyl]piperazin-1-yl }-1-phenylpropanone obtainable in Example 28 and sodium borohydride as a reducing agent. The yield of the hydrochloride of the compound was 62%.

Melting point: 160°–170° C.

Elementary analyses: as C$_{23}$H$_{22}$Cl$_2$N$_2$O$_2$ Found (%): C, 62.38, H, 7.16, N, 6.22 Calcd. (%): C, 62.87, H, 7.29, N, 6.39

DI-MS (m/e): 366(M$^+$)

IR (nujol) cm$^{-1}$: 3400

NMR (CD$_3$OD) δ: 2.00–2.50(2H, m), 2.73–3.10(2H, m), 3.50–4.40(15H, m), 7.21(4H, s), 7.43(5H, s)

EXAMPLE 30

1-(4-Hydroxyphenyl)-2-[2-(1,2,3,4-tetrahydro-1-naphthyl)-1-methylethylamino]ethanol (Compound 30)

Compound 30 was obtained as a powder in the same manner as in Example 1, using (1,2,3,4-tetrahydro-1-naphthyl)acetone [Chem. Pham. Bull., 36, 3453 (1988)] and 2-amino-1-(4-hydroxyphenyl)ethanol. The yield of compound 30 was 54%.

IR (nujol) cm$^{-1}$: 3180

NMR (CDCl$_3$) δ: 1.00 and 1.21(3H, d, J=6 Hz), 1.38–2.12 (6H, m), 2.34–3.33(6H, m), 4.37–4.91(1H, m), 5.39 (3H, bs), 6.70(2H, d, J=8 Hz), 6.89–7.40(6H, m)

EXAMPLE 31

1-(4-Hydroxyphenyl)-2-[1-methyl-2-(2-methyl-1,2,3,4-tetrahydroisoquinolin-1-yl) ethylamino]ethanol (Compound 31)

The same procedure as described in Example 1 was repeated, using (2-methyl-1,2,3,4-tetrahydroisoquinolin-1-yl)acetone [Synthesis, 1001 (1988)]and 2-amino-1-(4-hydroxyphenyl)ethanol, to give crude crystals. The crude crystals were washed with ether to give crystals of Compound 31 in a yield of 47%.

Melting point: 113°–115° C.

FAB-MS (m/e): 341(M$^+$ +1)

IR (nujol) cm$^{-1}$: 3220

NMR (CDCl$_3$) δ: 1.08 and 1.32(3H, d, J=6 Hz), 1.58–2.15 (2H, m), 2.20–2.15(10H, m), 3.61–4.10(1H, m), 4.71–5.16(1H, m), 5.70–6.51(2H, bs), 6.74(2H, d, J=8 Hz), 6.94–7.39(6H, m)

REFERENCE EXAMPLE 1

(Isochroman-1-yl)methyl chloride 8.4 g (70.6 mmol) of thionyl chloride was dropwise added to a solution of 10 g (61 mmol) of (isochroman-1-yl)methanol [J. Med. Chem., 28, 1026 (1985)] and 5 g (63 mmol) of anhydrous pyridine in dried benzene, and the resulting mixture was heated under reflux for 2 hours. Excessive amounts of thionyl chloride and benzene were evaporated, and the residue was dissolved in ether. The ethereal solution was washed with water and dried, and the solvent was then evaporated. The residue was distilled under reduced pressure (140° C./20 mmHg) to give 10.9 g (98%) of the desired compound as an oily.

NMR (CDCl$_3$) δ: 2.50–3.40(2H, m), 3.41–4.80(4H, m), 4.95–5.30(1H, m), 7.20(4H, s)

REFERENCE EXAMPLE 2

1-[(Isochroman-1-yl)methyl]piperazine

To 1 g (5.48 mmol) of (isochroman-1-yl)methyl chloride obtainable by Reference Example 1 was added 2 g (23.3 mmol) of piperazine, and the resulting mixture was heated at 100° to 120° C. for 10 hours. After being cooled, the mixture was basified with the addition of 10% sodium hydroxide and then extracted with chloroform. The extract was washed with water and then dried. The solvent was evaporated off. The residue was distilled under reduced pressure (150° C./15 mmHg) to give 0.9 g (74%) of the desired compound as an oily.

DI-MS (m/e): 364(M+)

IR (nujol) cm$^{-1}$: 3200

NMR (CDCl$_3$) δ: 2.40–3.20(12H, m), 3.30–4.70(3H, m), 4.95(1H, t, J=6 Hz), 7.30(4H, s)

Pharmaceutical Preparation 1 (Tablet)

A tablet having the following components is prepared in a conventional manner.

Compound 30: 30 μg
Lactose: 60 mg
Potato starch: 30 mg
Polyvinyl alcohol: 2 mg
Magnesium stearate: 1 mg
Tar pigment: q.s.

Pharmaceutical Preparation 2 (Powder)

A powder comprising the following components is prepared in a conventional manner.

Compound 30: 30 μg
Lactose: 270 mg

Pharmaceutical Preparation 3 (Syrup)

A syrup comprising the following components is prepared in a conventional manner.

Compound 30: 300 μg
Purified surcrose: 40 g
Methyl p-hydroxybenzoate: 40 mg
Propyl p-hydroxybenzoate: 10 mg
Strawberry flavor: 0.1 cc Water is added to the above components until the total volume is 100 cc.

What is claimed is:

1. An arylalkylamine compound represented by the formula (I)

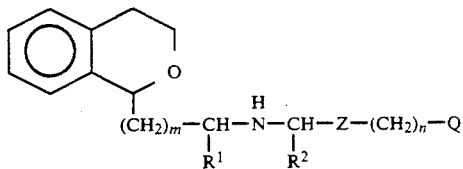

wherein
Z represents

in which R$^4$ represents hydrogen or lower alkyl or

Q represents phenyl or naphthyl which is optionally substituted with 1 to 3 substituents independently selected from the group consisting of lower alkyl, hydroxyl, lower alkoxyl, halogen and trifluoromethyl; each of R$^1$ and R$^2$ independently represents hydrogen or lower alkyl;
each of m and n independently represents 0 or 1; or a pharmaceutically acceptable salt thereof.

2. A compound according to claim 1 wherein Z is

and Q is a 4-hydroxyphenyl.

3. (1R)-1-(4-Hydroxyphenyl)-2-[2-(isochroman-1-yl)-1-methylethylamino]ethanol or a pharmaceutically acceptable salt thereof.

4. A compound according to any one of claims 1 and 3, wherein said salt is an inorganic acid salt selected from the group consisting of hydrochloride, sulfate and phosphate, or an organic acid salt selected from the group consisting of acetate, maleate, fumarate, tartrate and citrate.

5. A pharmaceutical composition comprising a pharmaceutical carrier and as an active ingredient, a bronchodilatorily or antiallergically effective amount of the compound as defined by claim 1.

* * * * *